(12) United States Patent
Minoretti et al.

(10) Patent No.: US 7,347,687 B2
(45) Date of Patent: Mar. 25, 2008

(54) DISTRACTION APPARATUS FOR ORTHODONTIC, ORTHOGNATHIC AND ORAL/MAXILLOFACIAL SURGERY APPLICATIONS ON THE MANDIBLE

(76) Inventors: Roger Minoretti, Moehrlistrasse 63, CH-8006 Zurich (CH); Albino Triaca, Germaniastrasse 47, CH-8006 Zurich (CH); Beat Merz, Max Daetwylerstrasse 12, CH-8126 Zumikon (CH); Reto Baumgartner, Bifangstrasse 11, CH-4412 Nuglar (CH); Thomas Bruderer, Fotschengasse 9, CH-8215 Hallau (CH); Roger Von Mentlen, Buetzbergstrasse 21, CH-8427 Rorbas (CH)

( * ) Notice: Subject to any disclaimer, the term of this patent is extended or adjusted under 35 U.S.C. 154(b) by 64 days.

(21) Appl. No.: 10/502,213

(22) PCT Filed: Jan. 23, 2003

(86) PCT No.: PCT/EP03/00688

§ 371 (c)(1), (2), (4) Date: Sep. 17, 2004

(87) PCT Pub. No.: WO03/061493

PCT Pub. Date: Jul. 31, 2003

(65) Prior Publication Data

US 2005/0130092 A1    Jun. 16, 2005

(30) Foreign Application Priority Data

Jan. 23, 2002    (CH) .................................... 0110/02

(51) Int. Cl.
*A61B 17/66* (2006.01)

(52) U.S. Cl. ......................................... 433/7; 606/105

(58) Field of Classification Search ................ 433/7, 433/24; 606/105, 70, 71, 90
See application file for complete search history.

(56) References Cited

U.S. PATENT DOCUMENTS

| | | | | |
|---|---|---|---|---|
| 4,433,956 A | * | 2/1984 | Witzig ............................ 433/7 |
| 5,364,396 A | * | 11/1994 | Robinson et al. ............. 606/53 |
| 5,775,907 A | * | 7/1998 | Razdolsky ................... 433/173 |
| 5,829,971 A | * | 11/1998 | Razdolsky et al. ............ 433/7 |
| 5,855,580 A | * | 1/1999 | Kreidler et al. ............... 606/71 |
| 5,885,290 A | * | 3/1999 | Guerrero et al. .............. 606/71 |
| 5,911,574 A | * | 6/1999 | Casey .......................... 433/19 |
| 5,993,448 A | * | 11/1999 | Remmler ...................... 606/53 |
| 6,050,819 A | * | 4/2000 | Robinson .................... 433/173 |

(Continued)

FOREIGN PATENT DOCUMENTS

CH    693 557 A5 *   7/1998

(Continued)

*Primary Examiner*—Ralph A. Lewis
(74) *Attorney, Agent, or Firm*—Milde & Hoffberg, LLP

(57) ABSTRACT

The invention concerns a distraction appliance for orthodontic, orthognathic and maxillofacial surgery purposes on the mandible for the distraction of a frontal bone segment, wherein the appliance is formed by a first distractor module and a second distractor module, wherein the first distractor module is essentially u-shaped, approximated to a dental arch, and has a mid-segment and on both sides of it an end-segment, wherein the corresponding end-segment is connected to the mid-segment by means of a linear distraction element and wherein each end-segment provides fixation parts, and wherein the second distractor module is related to a frontal bone segment to be moved, guiding the same and having fixation parts.

24 Claims, 9 Drawing Sheets

U.S. PATENT DOCUMENTS

| | | | |
|---|---|---|---|
| 6,053,919 A * | 4/2000 | Talos et al. .................... | 606/71 |
| 6,325,803 B1 * | 12/2001 | Schumacher et al. ......... | 606/71 |
| 6,358,255 B1 * | 3/2002 | Testa .......................... | 606/105 |
| 6,423,069 B1 * | 7/2002 | Sellers ........................ | 606/71 |
| 6,589,250 B2 * | 7/2003 | Schendel .................... | 606/105 |
| 6,666,867 B2 * | 12/2003 | Ralph et al. ................. | 606/71 |

FOREIGN PATENT DOCUMENTS

| | | |
|---|---|---|
| EP | 1 147 745 A2 * | 4/2001 |
| WO | WO 02/89682 A1 * | 5/2002 |

* cited by examiner

DISTRACTION APPARATUS FOR ORTHODONTIC, ORTHOGNATHIC AND ORAL/MAXILLOFACIAL SURGERY APPLICATIONS ON THE MANDIBLE

BACKGROUND OF THE INVENTION

The present invention relates to a distraction apparatus for orthodontic, orthognathic and oral/maxillofacial surgery applications on the mandible which is used for distraction osteogenesis of a dentate anterior bone segment.

The present distraction apparatus has its application in orthodontics, orthognathic surgery and general oral and maxillofacial surgery. It is its purpose to provide the surgeon with a tool to distract bony segments, e.g. in the area of the anterior mandible. In particular, such an apparatus should enable the surgeon to achieve a more prominent chin or to translate an anterior bone segment including the integrated teeth and to change its dental axis, if required.

In oral/maxillofacial surgery there is often the need to precisely move a bony segment gradually, to rotate it into a different position or to combine both movements. Thereby, the movement is achieved over several days after the osteotomy in the sense of a so-called callus distraction.

One application is genioplasty, where the anterior lower edge of the mandible is detached and reattached in a more advanced position by means of osteosynthesis screws; the goal of this procedure is to increase the prominence of the chin, e.g. in the case of a too posterior position, in order to provide the patient with a more aesthetic facial profile. Typically, this movement is done in one step which may result in discontinuities in the bony profile at the osteotomy site and therefore also the soft tissue profile of the lower mandibular edge. Furthermore, the soft-tissue in the area of the chin are heavily stretched and strained in a one-step translation.

In another application there is the need, to loosen an anterior segment of the alveolar ridge with the included dentition and to move this segment more to the front and/or to rotate it, e.g. to gain more space for the teeth in the case of an anterior dental crowding, or to provide some more length to a mandible which is slightly to short relative to the maxilla, in order to achieve an improved occlusion. Such movements were also done in one step, in the past. This has the disadvantage that it limits the achievable movement since sufficient overlapping between the osteotomy surfaces has to be retained. Furthermore also here the soft tissues are heavily stretched which can result in dehiscence of the mucosa in the area of the osteotomy.

SUMMARY OF THE INVENTION

It is the object of the present invention to prevent the described disadvantages of current appliances and methods and in particular to provide an apparatus which enables the desired corrections of the mandible with respect to a frontal bone segment.

This object is achieved by means of a distraction apparatus for orthodontic, orthognathic and oral/maxillofacial surgery in the mandible with the purpose of distracting a dentate frontal bone segment. This distraction apparatus is characterized by being construed from a first module and a second module where the first module essentially has a U-shape approximating the dental arch and features a middle section and on both sides thereof an end-section where the corresponding end-section is connected to the middle-section via a linear distraction element and where each end-section includes fixation means, and where the second module which has fixation parts can be assigned to an anterior bony segment to fixate it.

With the present apparatus it is possible to achieve a gradual displacement of a frontal bone segment in the sense of a callus distraction. The distraction is done continuously by distracting by means of the two distraction modules in short time intervals. The second distraction module serves the purpose of rotating the frontal bone segment in the sagittal plane.

With the inventive apparatus a gradual displacement respectively pivoting or rotation of the frontal bone segment into a desired position is possible; in comparison to previous surgical methods, a longer movement distance can be achieved, as by the continuous distraction by means of the two linear distraction modules the soft-tissues can adapt to the changed bone geometry during the course of the distraction. Furthermore, the connection by the callus makes an overlap of the osteotomy surfaces unnecessary.

In one embodiment of the distraction apparatus, the corresponding end segments of the first distractor module have fixation elements for the fixation of lateral teeth.

These end segments of the first distractor module can contain fixation elements for a fixation by means of bone screws on the mandible.

In a preferred embodiment of the distraction apparatus, the corresponding distraction element which connects the mid-segment with the end-segment of the first distractor module is constructed from at least three elements which are connected to each other. Thereby, the first element takes the form of a sleeve and inside of it the second and third element are pivoted, where the second and the third element are screwed into the first element with threads in opposite rotation sense such that under rotation of the first element in one or the other sense the distraction element is shortened or lengthened.

In order to make the distraction device easy to handle for the surgeon, there is a section point in the area of the corresponding distraction element. In the area of this section point the end segment can be solved or separated from the mid-segment. Therefore, it possible that the surgeon first connects the end segment on the jawbone of the patient and only then connects and fixates the distraction elements and the mid-segment.

Besides of a fixation of the end-segments on the jawbone with bone screws it is also possible to fixate the end-segments on the teeth, for example with a clips or clamps. A further fixation possibility of the end-segments is to screw them on by the help of a pin with single-sided threat, where on the other end opposed to the thread a sleeve or tube is mounted into which the end-segment of the first distractor module is inserted. Such a fixation with a sleeve or a tube can also be achieved by fixating it, e.g. welding it to a metal band which is positioned around a tooth and whereby the axis of the sleeve or tube is about horizontal. Into this sleeve or tube the end-segment of the first distractor module can be inserted and if desirable fixated.

The second distractor module can take the form of a hinge with two hinge parts where one hinge parts is related to the mandibular and the other is related to the frontal bone segment to be distracted.

The hinge axis should preferably run about parallel to the occlusal plane and vertical to the sagittal plane.

In order to alleviate the use of such a hinge, it can contain a stop position to limit the pivoting range of the hinge parts, such that the hinge can only be rotated in the required rotation sense in order to correct the axis of the frontal bone segment.

The fixation parts of the second distractor module can be formed by drill holes. Such drill holes can take the form of a slotted hole or several slotted holes such that in the area of the slotted holes a variable fixation point is possible which can be selected by the surgeon during the operation according to his needs.

Such a slotted hole can be formed by overlapping drill holes such that discrete fixation positions are defined.

In a further embodiment of the second distractor module, a guiding sleeve is inserted into the slotted hole, which is movable along the slotted hole; such a guiding sleeve has a drill hole or a slot, into which a fixation screw can be inserted with which a fixation of the guiding sleeve on the frontal bone segment is possible. Such a guiding sleeve could also take a form which makes it possible to clamp it into the slotted hole.

For a shifting of moving of the guiding sleeve and therefore of the bone segment fixated thereto, a linkage inserting into it can be arranged. With the help of this linkage, the part of the second distractor module which carries the guiding sleeve can be rotated about the hinge axis. Such a linkage can be tautened by a screwing element held in a bearing, such that a tensile force is exerted onto the guiding sleeve. By tautening of this linkage, a translation of the segment relative to the guiding sleeve and to the hinge can be achieved. Then a rotation about the axis can be achieved by means of springs of similar parts fixated on the dentition.

In a further embodiment one of the hinge halves of the second distractor module is formed in a V-shape in order to arrange a fixation part on each of the free end of the both legs. In connection with such a V-shaped arrangement of one of the hinge halves an additional fixation point can be provided at the area of junction of the both legs.

A further preferable embodiment of the distraction apparatus is obtained if the second distractor module is swivel-mounted and/or pivoting on the first distractor module and is in a fix relation relative to it. From the surgical point of view, this embodiment is then preferable, if the whole anterior corpus (the complete dentate front segment of the mandible including the chin) is to be moved towards anterior, where, depending on the facial profile, the chin needs to be moved more anterior then the incisal edge of the anterior mandibular dentition.

In the above mentioned further embodiment, the second distractor module can take the form of a cantilever, where in this cantilever is then connected to the mid-segment of the first distractor module and wherein on the cantilever there are fixation means provided for the frontal bone segment.

Furthermore, in this further embodiment the second distractor module can be an U-shaped cantilever with two legs and a mid-segment connecting the two legs, wherein the mid-segment is connected to the mid-segment of the first distractor module and wherein the free ends of the two legs have fixation means.

The second distractor module can also be an essentially beam-shaped cantilever which has on the free end fixation means.

For a distraction of the frontal bone segment in craniocaudal direction, the cantilever can be lengthened or shortened by means of an adaptation mechanism; such an adaptation mechanism my contain a spindle drive with shaft joint.

For a full understanding of the present invention, reference should now be made to the following detailed description of the preferred embodiments of the invention as illustrated in the accompanying drawings.

BRIEF DESCRIPTION OF THE DRAWINGS

FIG. 5a shows a further embodiment of the hinge-like second distractor module for the advancement of the chin (genioplasty).

FIG. 5b shows a side view of the distractor in FIG. 5a in an anatomic arrangement for the advancement of the chin in the context of a genioplasty.

FIG. 5c shows the same embodiment as FIG. 5b in a front view prior to the begin of the distraction.

DESCRIPTION OF THE PREFERRED EMBODIMENT

Figure 1A:
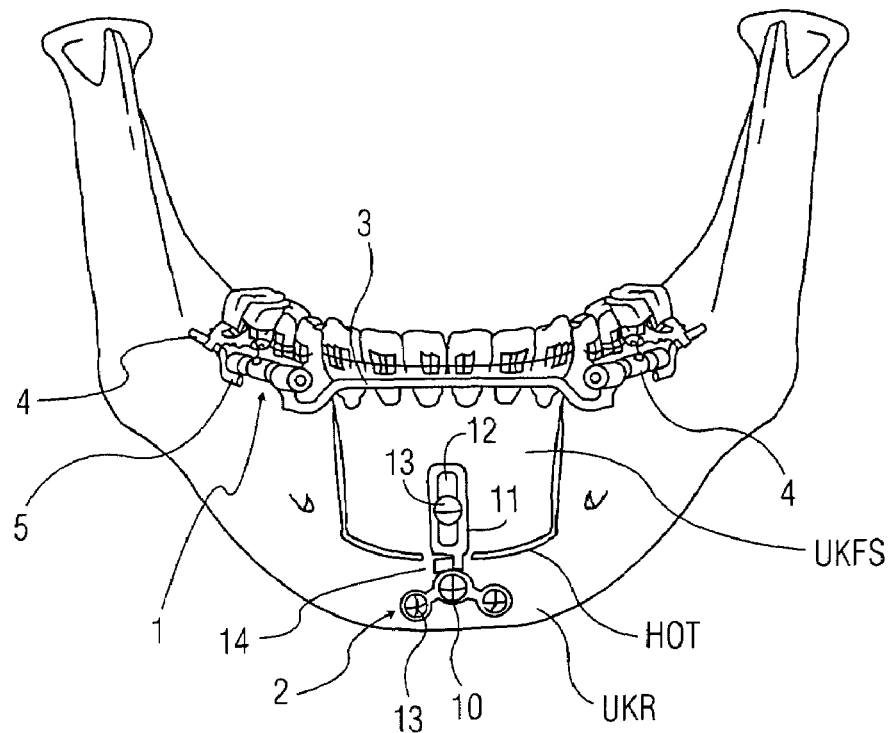
FIG. 1a shows a frontal view of a first embodiment of a distractor for the distraction of a frontal bone segment with a first distractor module running along the dental arch and a second distractor module, where the second distractor module takes the shape of a hinge.

The preferred embodiments of the present invention will now be described with reference to FIGS. 1-9 of the drawings. Identical elements in the various figures are designated with the same reference numerals.

Figure 1B:
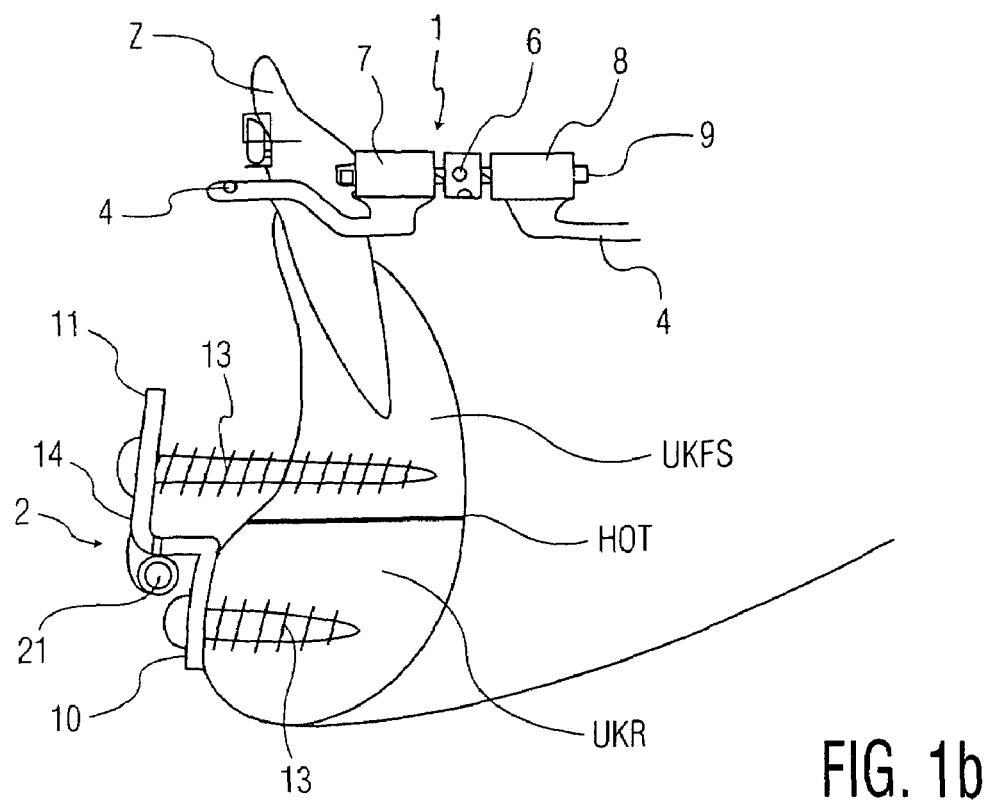
FIG. 1b shows a side view of the arrangement in FIG. 1 seen from the point of view 1b in FIG. 1a, prior to the begin of the distraction.

FIG. 1a shows a first embodiment of a distractor for orthodontic/orthognathic and maxillofacial surgery purposes on the mandible for the distraction of a frontal bone segment which, as depicted in FIG. 1a, contains the corresponding frontal teeth; the distractor is nevertheless also then applicable, if the frontal dentition is not present. The distractor encloses a first distractor module 1 and a second distractor module 2. The first distractor module 1 shows an essentially U-shaped form, approaching the dental arch and includes a mid-segment 3 as well adjacent on both sides a respective end-segment 4. Between each end-segment 4 and the mid-segment 3 there is a linear distraction element 5 inserted. Such a linear distraction element is constructed—as also clarified in FIG. 1b—from a first element 6 and a second and third element 7 and 8, respectively. The first element 6 is a sleeve-shaped part with a threaded beam 9 pivoting inside of it, which extends on both sides of the first element 6, with a thread in opposing rotation sense, respectively. The two threads with opposing rotation sense are inserting into corresponding female threads of the corresponding second and third element 7 and 8. As can be seen in FIG. 1b, the first element 6 has drill holes into which a tool can be engaged to rotate the first element 6 and therefore the threaded beam 9.

It should be pointed out, that the linear distraction element 5, as it is depicted in the figures, also may feature a composition in contrast to the depicted embodiments, in which the middle, first element 6 has a sleeve with two counter rotational female thread portions, into which the second and third element 7 and 8, taking the form of male threaded beams are screwed in. When rotating the first element 6 in one or the other direction, the linear distraction element 5 can be shortened or lengthened.

The two end-segments 4 of the first distractor module 1 are fixated to one or several suitable teeth by means of connection to a metal band which is positioned around such teeth.

The mid-segment 3 is also connected to the frontal dentition as evident in FIGS. 1a and 1b.

The second distractor module 2 takes in the embodiment depicted in FIGS. 1a and 1b the form of a hinge 14 with a first, lower hinge-half 10 and a second upper hinge-half 11. The lower hinge-half 10 furthermore includes two legs with each featuring a hole for bone screws on both ends and a screw hole on the connection of both legs. The second, upper hinge-half 11 takes the form of a single leg which has a slotted hole 12 for the connection by a bone screw.

The lower hinge-half 10 is screwed to the mandibular bone by means of customary bone screws, marked 13 in all figures. The upper hinge-half 11, however, is screwed to a loose mandibular bone segment as depicted in FIG. 1a.

It should be pointed out that the second distractor module having the form of a hinge 14 has a stop position 15, which can be seen in the side view of the hinge 14 in FIG. 1b. This stop position is formed by a leading edge of the lower hinge-half 10 against which the second, upper hinge-half 11 abuts, such that a rotation of both hinge-halves 10, 11 seen from the direction of the upper hinge-half 11, is limited in the clockwise direction. Such a stop position is helpful for the surgeon to maintain the base position as depicted in FIG. 1b.

By means of the slotted hole 12 in the upper hinge-half 11 the second distractor module can be moved in a certain range and can therefore be adapted to the specific circumstances in order to serve as bearing for a bone screw in a certain range of heights. As can be seen in the side view of FIG. 1b, the upper hinge-half 11 is shifted in its longitudinal axis relative to the lower hinge-half 10, in order to provide sufficient space for an advancement of a bone segment, the motion path being defined by the free thread portion of screw 13 in FIG. 1b. This embodiment is also elucidated in the enlarged depiction of FIG. 1c.

While one leg 11 of the hinge 14 is screwed to the frontal bone segment of the mandible UKFS which has be cut off along an osteotomy line HOT, the other lower hinge-half 10 is screwed to the anterior lower mandibular rim UKR. It is important to note that besides of the screw 13, which is held in the upper hinge-half 11 and holds the frontal bone segment of the mandible UKFS, the frontal bone segment remains connected to the remaining mandible also through the soft tissues which are not shown in the drawing, as well as through the first distractor module 1, which is fixated as already mentioned above on the dentition.

Based on this construction of the distractor, the possibility of a linear distraction is given by means of the two distraction elements 5, which are related to the first distractor module 1, besides of a rotation of the mandibular front segment UKFS against the lower mandibular rim UKR by means of the second distractor module 2 which takes the form of a hinge 14. Although the two distractor elements 5 which are relating to the first distractor module 1 are not oriented in a parallel fashion, the movement of the mid-segment 3 when prolonging the distraction element 5 creates no problems due to the elasticity of the wire appliances which are held on the teeth by means of orthodontic brackets. The distractor is shown in FIGS. 1a and 1b in an initial position before start of the active distraction.

Also, in the drawings the acronyms UKR (lower mandibular rim), HOT (horizontal osteotomy line) and UKFS (anterior mandibular bone segment) are used while SZK stands for incisal edge of the incisors.

Based on this construction of the distractor, the possibility of a linear distraction is given by means of the two distraction elements 5, which are related to the first distractor module 1, besides of a rotation of the mandibular front segment UKFS against the lower mandibular rim UKR by means of the second distractor module 2 which takes the form of a hinge 14. Although the two distractor elements 5 which are relating to the first distractor module 1 are not oriented in a parallel fashion, the movement of the mid-segment 3 when prolonging the distraction element 5 creates no problems due to the elasticity of the wire appliances which are held on the teeth by means of orthodontic brackets. The distractor is shown in FIGS. 1a and 1b in an initial position before start of the active distraction.

It should be pointed out, that the same reference numbers are used for comparable elements in the single figures as far as they show identical or similar embodiments.

Also, in the drawings the acronyms UKR (lower mandibular rim), HOT (horizontal osteotomy line) and UKFS (anterior mandibular bone segment) are used while SZK stands for incisal edge of the incisors.

Figure 1C:
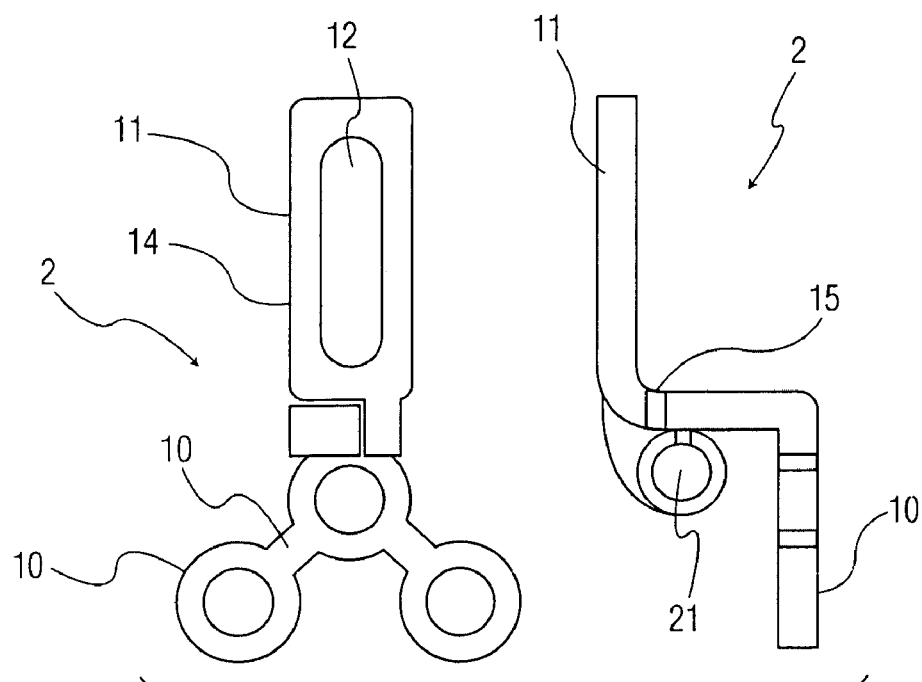
FIG. 1c shows the second distractor module of FIG. 1 in an enlarged depiction, in a top view and also in a side view.
Figure 1D:
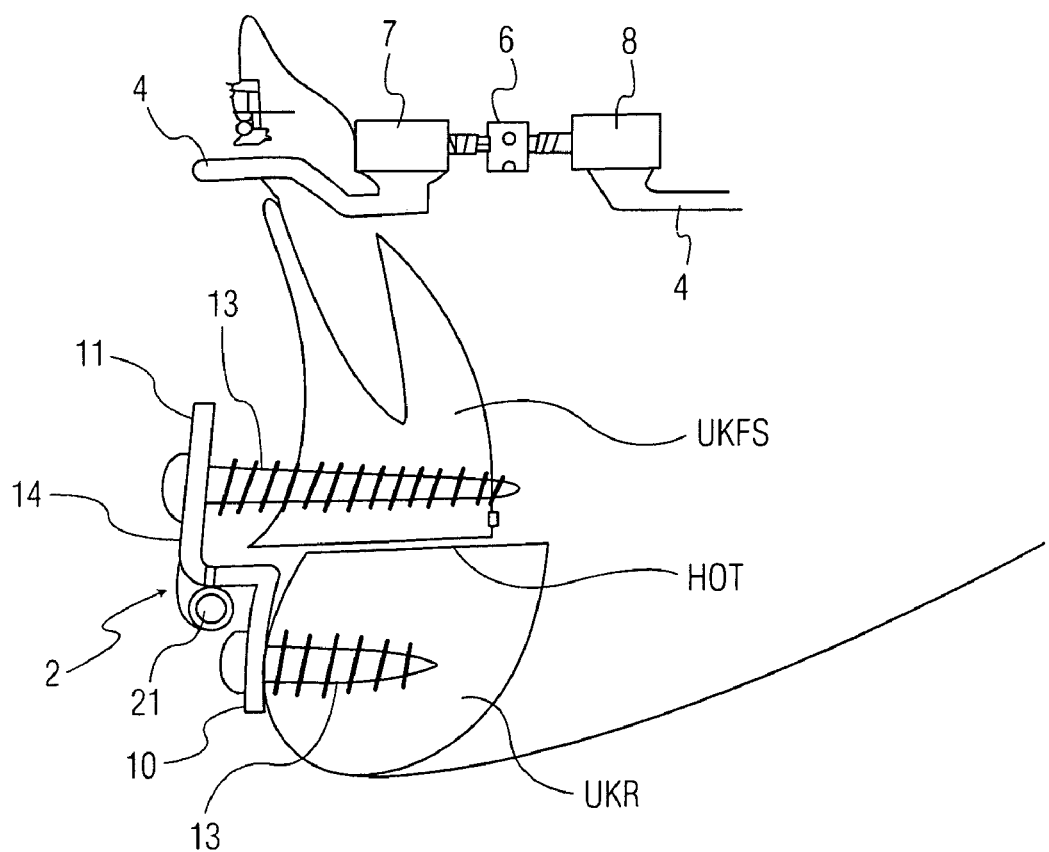
FIG. 1d shows a view, comparable to the one in FIG. 1b, but in a translatory phase.

In FIG. 1d a gradual, translational advancement of the front segment is shown. This movement is manly achieved by turning of the bone screw 13 which is assigned to the upper hinge-half 11. By rotating the bone screw 13 in clockwise direction it advances into the bone segment (UKFS) and therefore pulls it towards anterior. The advancement starts about 5-7 days after the osteotomy, whereby the daily advancement movement is 0.5-1 mm. Simultaneously, the orthodontic first distractor module 1 is activated by means of the two distraction elements 5 in such a manner that a translation along the horizontal osteotomy surface (HOT) is taking place. Therefore, the distraction is done as shown again in FIG. 1d by means of the distraction element 5, but also with the bone screw 13 which is relating to the upper hinge-half 11, by screwing it into the bone segment. The tightening of the bone screw 13 results in an advancement of the base of the bone segment. Simultaneously, the distraction elements effect a rotation of the segment about the hinge axis 21.

Figure 1E:
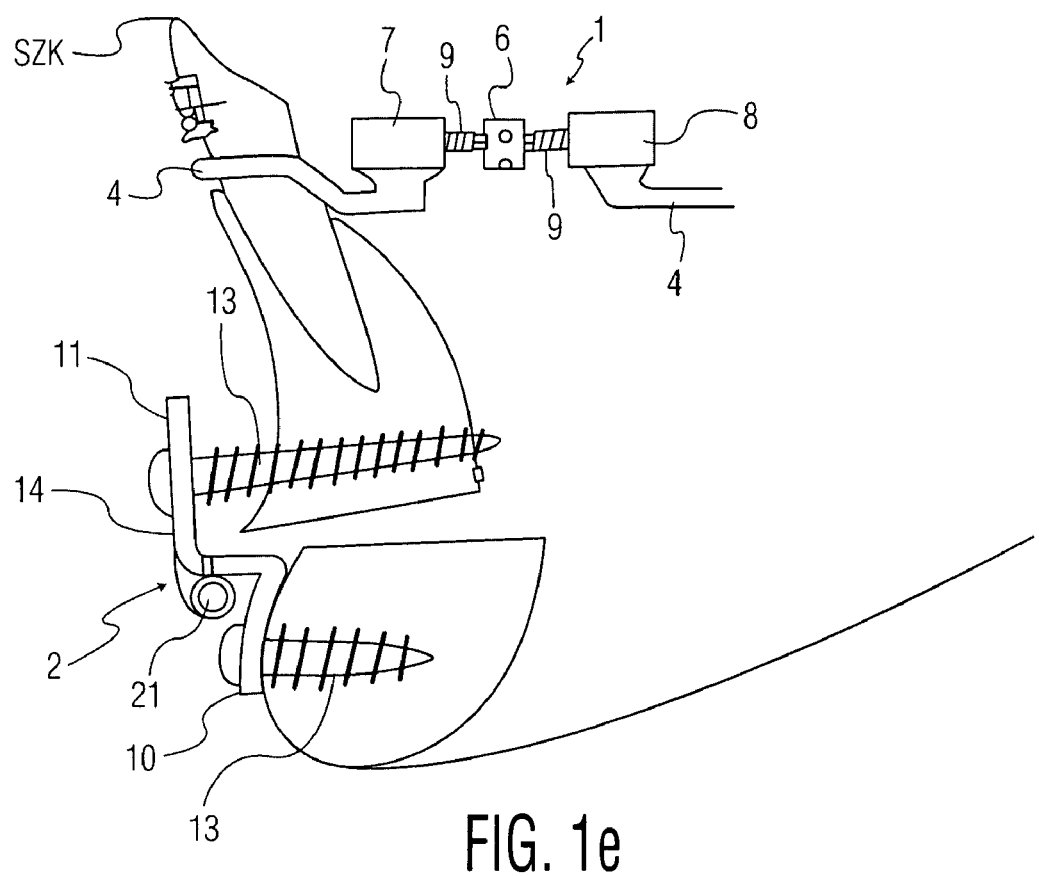
FIG. 1e shows a view corresponding to FIGS. 1b and 1d, towards the end of the treatment, after moving the bone segment towards anterior by translation and subsequent rotation about the hinge axis.

As depicted in FIG. 1e, it is possible to introduce subsequently to the translation (see FIG. 1d) a slight tilting of the bone segment by activating the distraction elements 5, which results in a further advancement of the incisal edge (SZK) and changes the dental axis. This may be desirable, for instance, if the dental axis was reclined too much towards posterior. The tilting movement is controlled exclusively by the first distractor module 1 with the distraction elements 5, while the upper bone screw 13 which is relating to the upper hinge-half 11 is usually not activated anymore.

Figure 2:
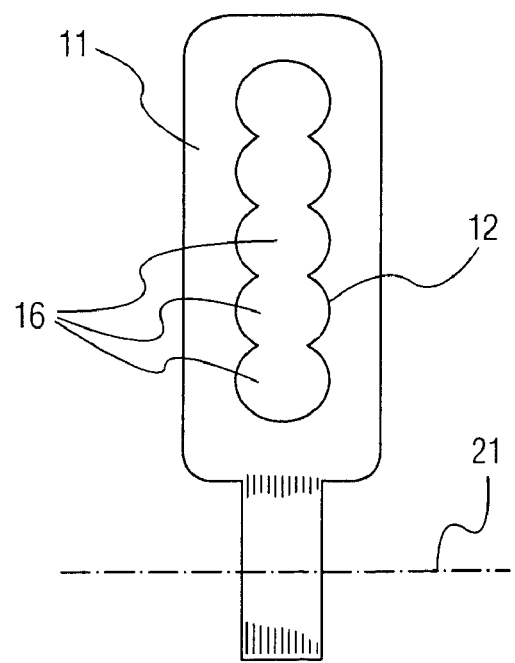
FIG. 2 shows a modified embodiment of the upper leg of the hinge-like second distractor module with different discrete positions guiding the bone screw.

FIG. 2 shows an embodiment of the second upper hinge-half 11 of the second distractor module. In this embodiment, the slotted hole of the upper hinge-half 11, as visible in FIGS. 1a and 1c, is replaced by several overlapping drill holes 16. These overlapping holes form several discrete positions in which the bone screw 13 can be inserted. Assuming a minimal thickness of the plate forming the upper hinge-half 11, it is also possible to give different axis directions to the overlapping drill holes, in order to add and additional slight vertical component to the translation.

Figure 3:
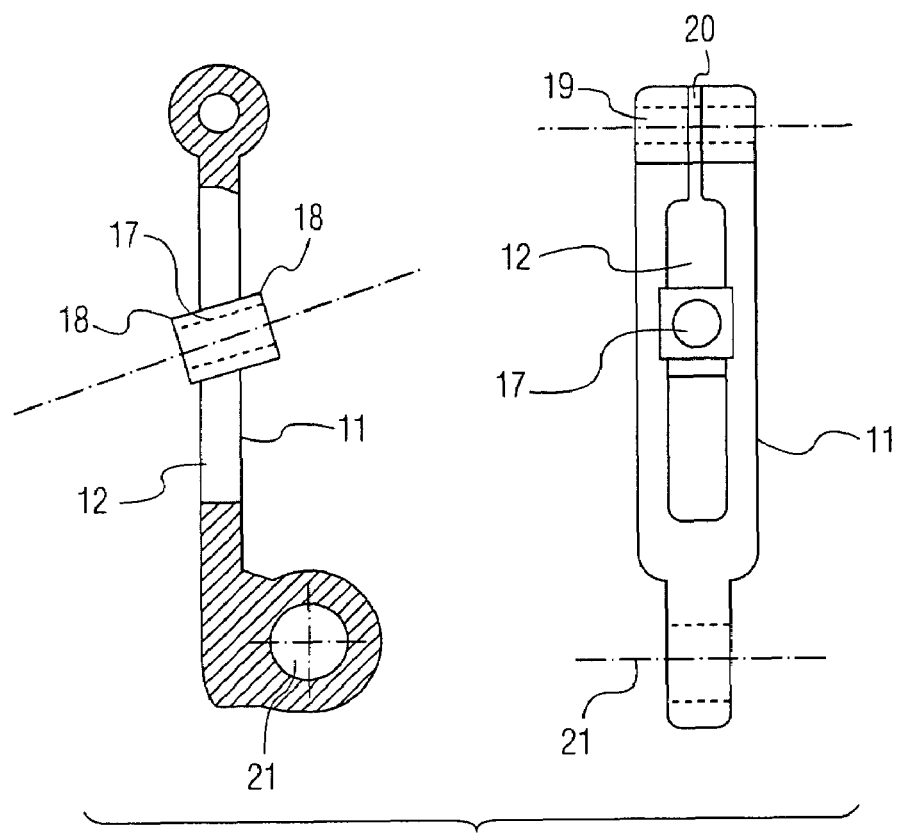
FIG. 3 shows a further variation of the upper segment of the hinge-like second distractor module with a guiding sleeve positioned in a slotted hole.

FIG. 3 show a further embodiment of the upper half 11 of the hinge 14 in a sectioned side view as well as in a top view. In this embodiment, the upper bone screw is guided by a guiding sleeve 17, which can be moved along a slotted hole 12, open on the upper end, and which can be clamped there in a certain range of positions and angulations. The guiding sleeve 17 has on both ends a slightly thicker diameter 18 which prevents the guiding sleeve 17 to drop out of the slotted hole 12. The clamping of the guiding sleeve 17 in the selected position is achieved by a clamping screw connection 19 which crosses a slot 20 on the upper end of the slotted hole 12 and compressed it. The axis of the hinge is marked 21 in FIG. 3.

Figure 4A:
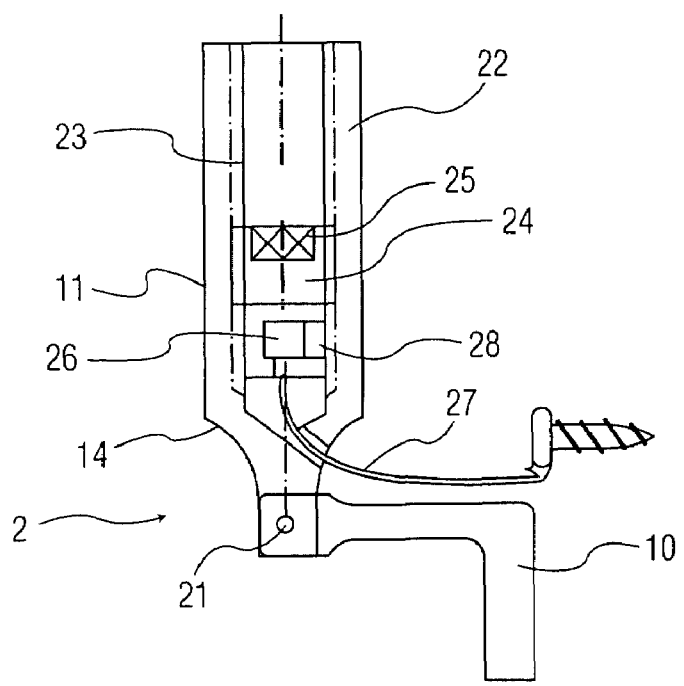
FIG. 4a shows a further variation of the upper segment of the hinge of the second distraction module, which contains an additional linkage with adaptation mechanism.

FIG. 4a shows a further embodiment of the second distractor module 2. In this embodiment, the advancement of the bone segment is not achieved by means of a screw which is screwed into the bone as depicted in FIGS. 1a to 1e, but by a cable linkage. The upper hinge-half 11 is formed in this embodiment by a hollow cylinder 22 with a female thread 23. Into the female thread 23 a short threaded pin 24 is inserted, which can be rotated from top through the opening of the hollow cylinder 22 by means of a not shown Allen wrench engaged in an internal hex 25. In the lower part of the threaded pin 24 a thickened end 26 of a cable linkage 27 is held; this thickened end is inserted into the threaded pin 24 through a lateral slot 28. Therefore, the thickened end 26 of the cable linkage 27 does not impede the rotation of the threaded pin 24. The cable linkage 27 is turned around in the lower area and lead to the outside and is connected on it free end to a bone screw 13.

Figure 4B:
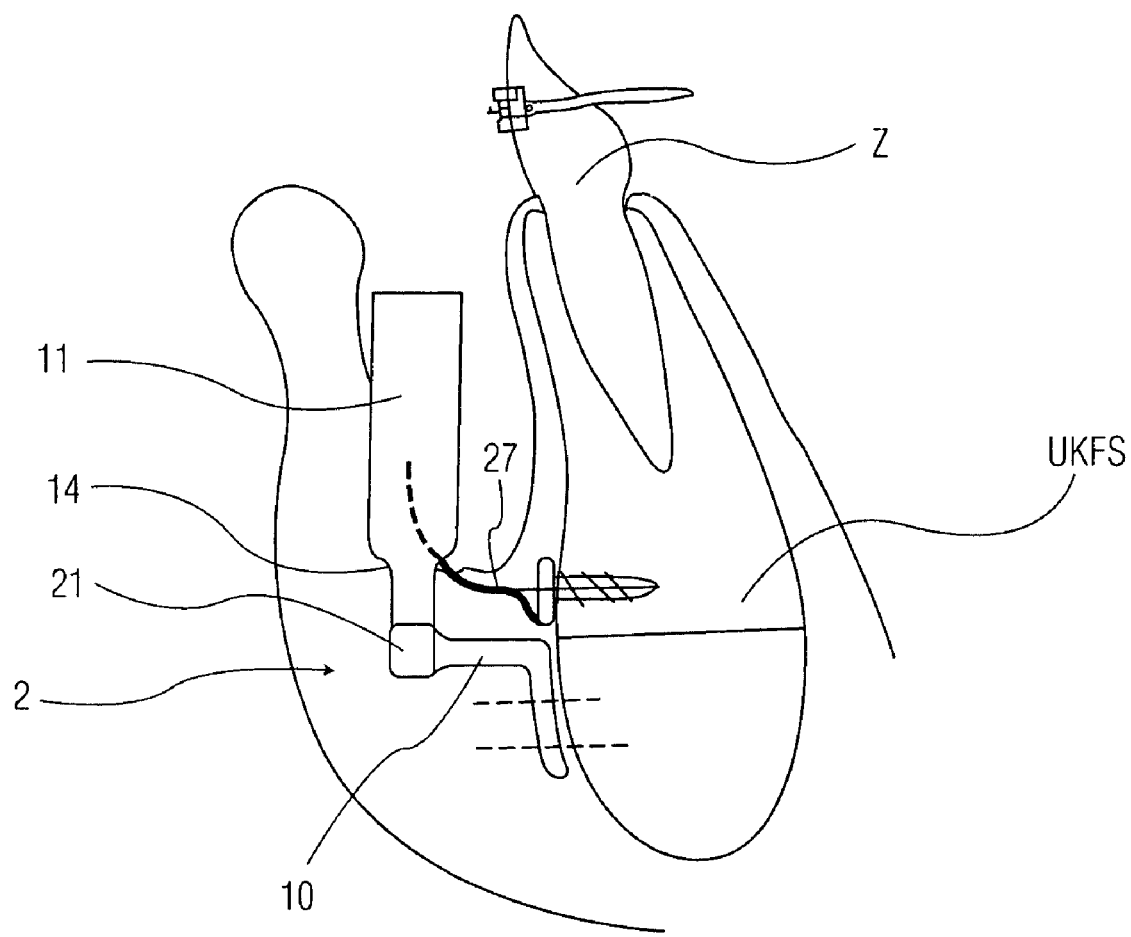
FIG. 4b shows the second distractor module of FIG. 4a schematically in an anatomic arrangement, seen in a side view.

FIG. 4b shows this second distractor module 2 as depicted in FIG. 4a, in an anatomical arrangement. The turned around cable linkage 27 is screwed to the bone segment UKFS by means of the bone screw 13 and can advance the bone segment towards anterior in the case of corresponding activation. Once the frontal bone segment has been advanced until reaching the upper hinge-half 11, it can subsequently be rotated around the hinge axis 21 guided on the dentition Z in analogous fashion to the embodiments described in FIGS. 1a-1e. In FIG. 4b the first distractor module of the distraction appliance is not depicted in detail, only a single bracket is shown as attached to dentition Z.

Figure 5:
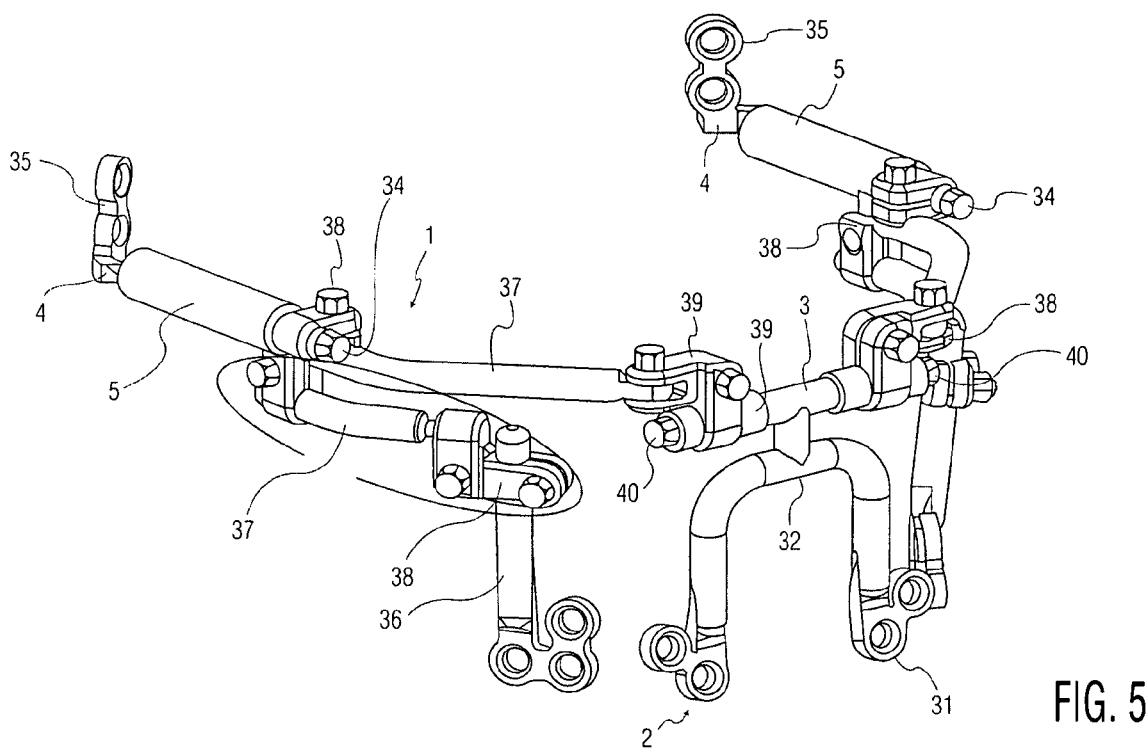
FIG. 5 shows a further embodiment of the distractor where the first distractor module and the second distractor module are directly connected to each other.

FIG. 5 is an embodiment of a further distraction appliance as example for the invention.

Figure 6:
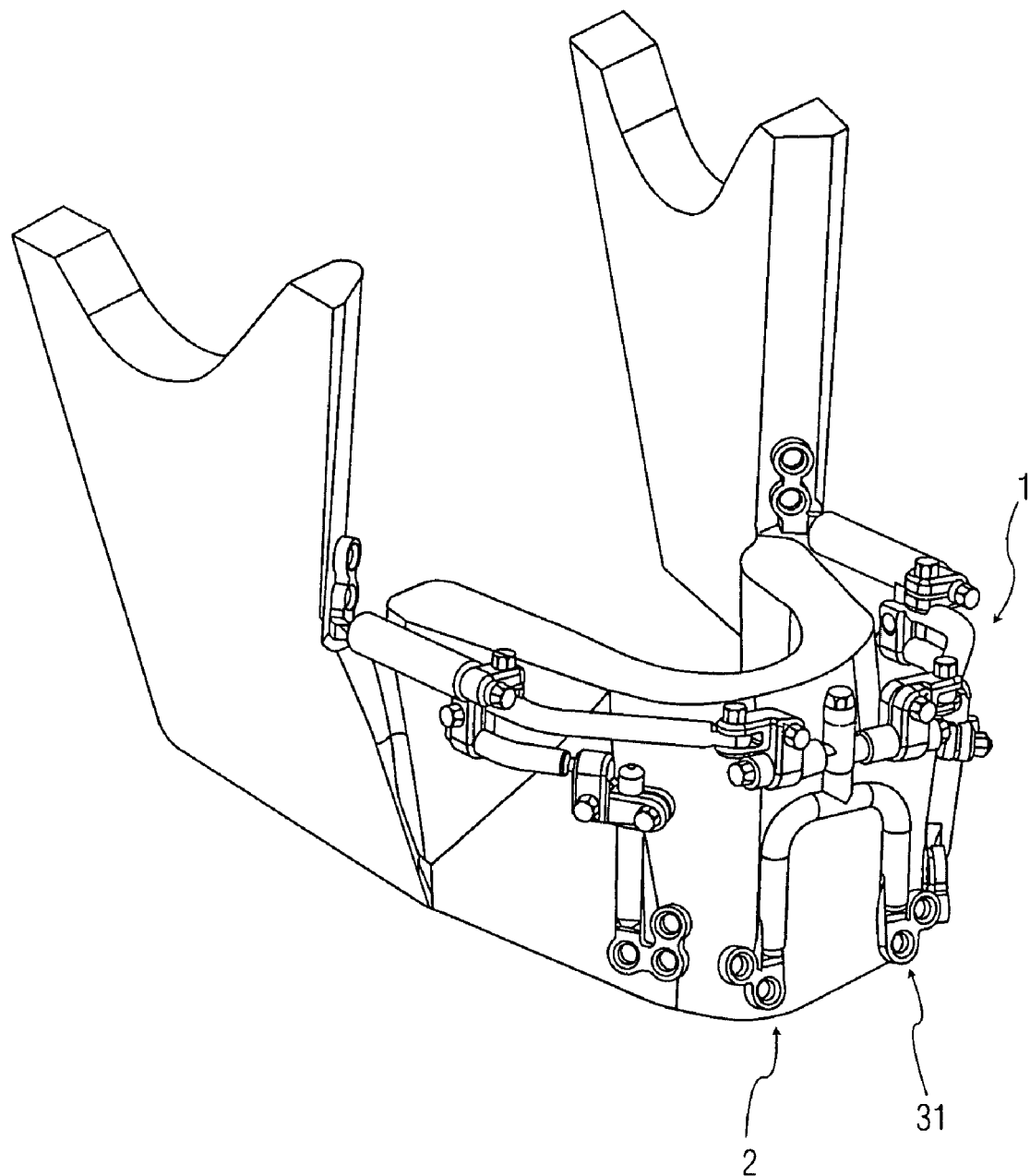
FIG. 6 shows the distractor of FIG. 6 as it is arranged on a schematically depicted mandible.

In this embodiment in FIG. 5, which is depicted in FIG. 6 arranged on a schematic mandible, again a first distractor module 1 and a second distractor module 2 are provided. The first distractor module 1 shows the typical U-shaped construction, which encompasses the mandible. In contrast to the embodiments described in the previous figures, the module has the form of an U-shaped cantilever 31, with two free legs and a transverse part 32. This U-shaped cantilever 31 is with its transverse part 32 connected to the mid-segment 3 of the first distractor module 1 by means of a connection 33.

In FIG. 5 the corresponding distraction element between the end-segment and the mid-segment is marked 5. The distraction is achieved by means of a threaded spindle engaged via screw head 34. Furthermore, in this appliance a connection to the ramus 35 is foreseen on the free end of the end-segment 4. The ramus connection 25 is designed such that it can be bent and adjusted during the operation in order to arrange the distraction element parallel to the sagittal plane. Further more a lateral anchorage 36 is provided, which serves as support for this first appliance part. The lateral anchorage 36 is inserted between the distraction element 5 and the mid-segment 3, parallel to an intermediate part 37. It is held by means of an unlockable clamp 38. The lateral anchorage 36 has an end-segment containing screw holes. The intermediate part 37 with the two clamping parts 38 on its both ends, is flexibly adaptable by means of unlocking clamps 38 in order to be able to adjust it the individual anatomy.

As mentioned, the U-shaped cantilever 31, which forms the second distractor module 2, is fixated to the osteotomised bone segment of the mandible with its free ends, for which purpose an each end of the u-shaped cantilever two fixation holes are provided.

In order to avoid discontinuities in the mandible such as corners or steps during a distraction towards ventral, this embodiment allows the creation of a natural shape of the mandible; the mandible can be spread in the anterior area. For this purpose further distraction elements 39 are inserted between the mid-segment 3 and the intermediate part 37; these linear distraction elements can be activated by means of the external hex 40. Furthermore, by means of the clamps which hold the two further distraction elements 39 on the intermediate parts 37 and the mid-segment 3, i.e. the U-shaped cantilever 31, an adjustment can be done. The U-shaped cantilever 31 is adjustable itself around the sagittal axis.

Figure 7A:
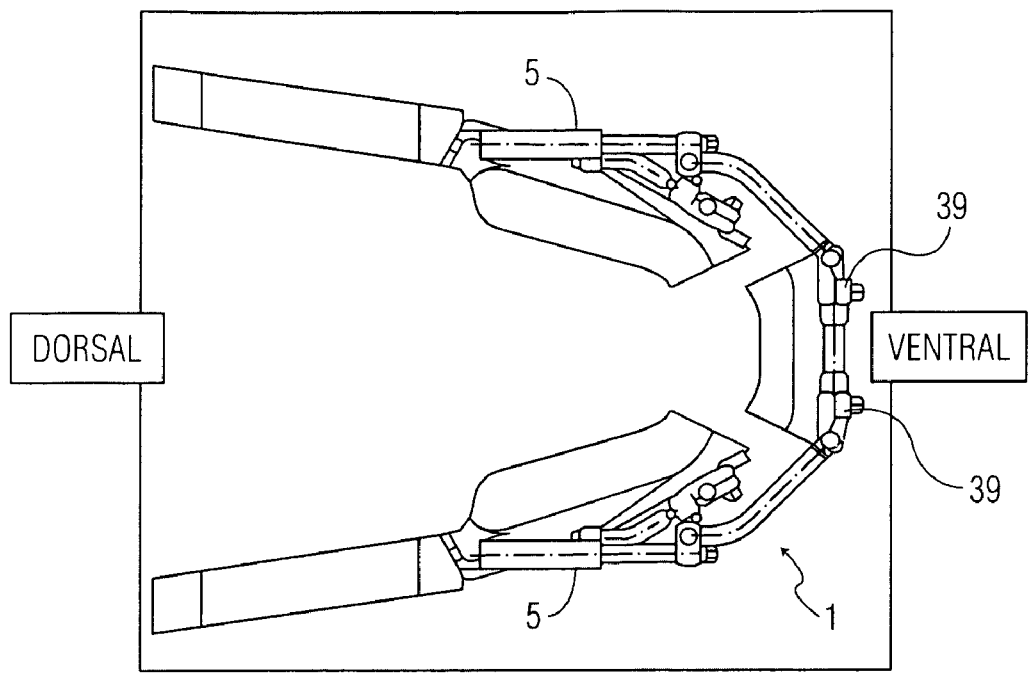
FIGS. 7a and 7b show the arrangement as depicted in FIG. 6, in a view cranial onto the mandible with a distraction in transversal direction.
Figure 7B:
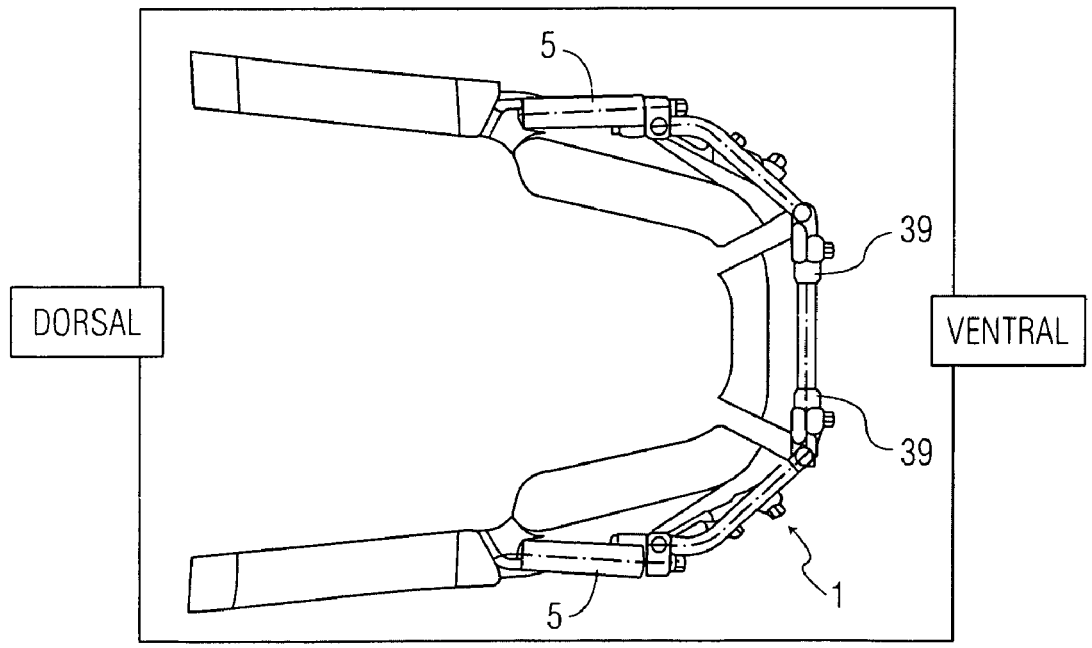

FIGS. 7a and 7b show a ventral as well as a transversal distraction.

In the ventral distraction with the appliance as shown in FIGS. 5 and 6, the bone segment is distracted towards ventral by activation of the two distraction elements 5. In FIG. 8a a distraction distance of maximal 12 mm is depicted where the distraction distance obtainable is dependent on the size of distraction element 5.

As can be seen in FIG. 7b, the form of the mandible can be adapted in transversal direction by means of the two anterior distraction elements 39. As indicated in the figure, a translation by 5 mm should achievable for each distraction element 39. During this transversal distraction, it should be noted that the mandible is also widened in lateral direction in the area of the temporo-mandibular joints. Therefore this has an impact on these joints which could be negatively affected. In order to avoid this, the screws on the section points respectively clamps 38 have to be loosened in order to allow an angular change in these connections and to unload the temporo-mandibular joints. After the translation, the screws in the clamps must be re-tightened in order to stabilize the system.

Figure 8:
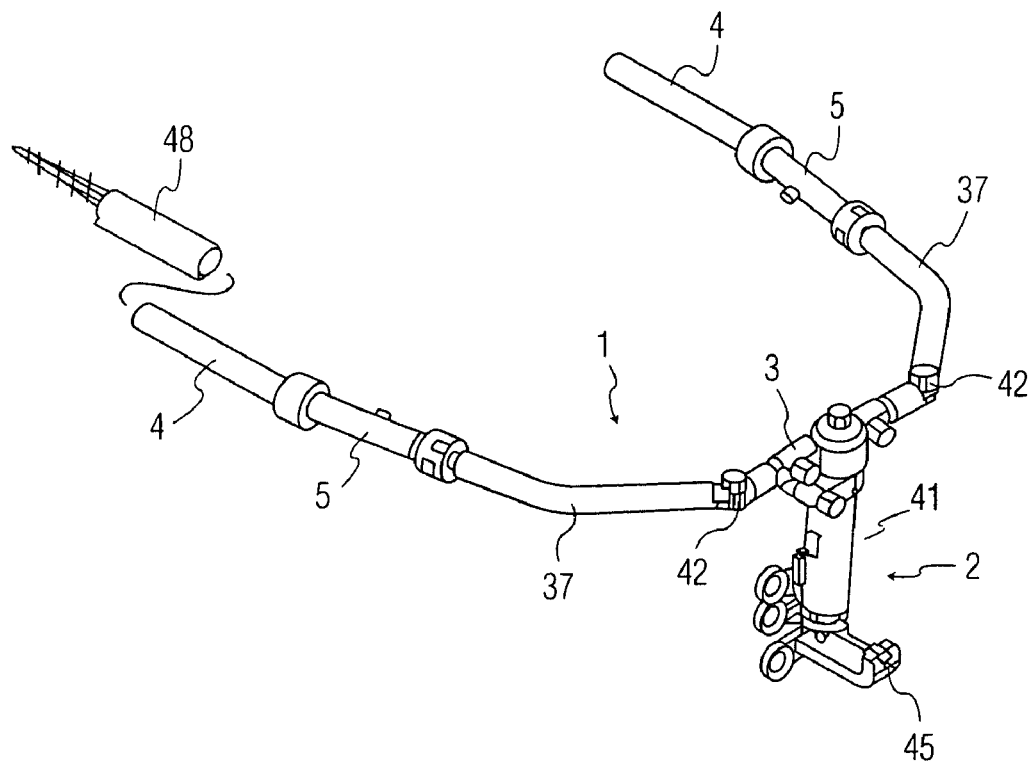
FIG. 8 shows a distractor, comparable to the one in FIG. 5, whereby, however, the second distractor module is in contrast to an U-shaped part built by a beam-like cantilever.
Figure 9:
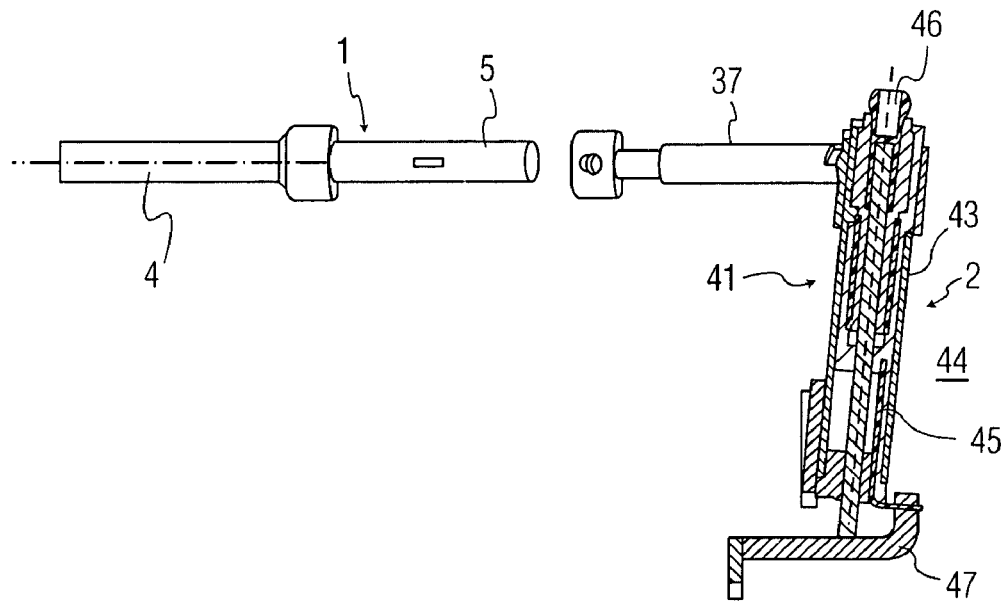
FIG. 9 shows the arrangement in FIG. 8 in a side view, where the beam-shaped cantilever is sectioned along its longitudinal axis.

A further distractor embodiment, comparable to the one in FIG. 5, is depicted in FIGS. 8 and 9. This distractor appliance in FIG. 8 features, in contrast to the U-shaped cantilever 31 in FIG. 5, an essentially beam-shaped cantilever 41. Again the distraction elements 5 are inserted between the end-segments 4 and an intermediate part 37. The mid-segment 3 of this appliance is connected to the intermediate part 37 by means of a simple joint connection 42. This joint connection 42 serves the purpose of counterbalancing a correction in the frontal plane. The beam-shaped cantilever 41 takes the form of a sleeve 43 with a beam 44 pivoting inside, as is shown in particular in FIG. 10 in the section. In the sleeve 43 furthermore a wire 45 is fixated, which is drawn towards cranial by the beam 44 respectively the screw 46 on the upper end. The lower end of the beam-shaped cantilever 41 is relating to a bearing and mount 47 for the wire 45, which bearing takes the shape of a part being bent in opposite directions on both ends. While the upper bent end holds the wire 45, the lower end bent towards below serves for the fixation to the bone. If the beam 44 is screwed into the screw 46 and therefore the beam 44 pressed onto the bearing 47, the whole frontal bone segment to which the upper part of the beam-shaped cantilever is fixated, is moved towards cranial. Therefore the wire 45 pulls the base of the frontal bone segment which is solved from the mandible towards anterior. The beam 44 pushes off at the bearing 47 and moves the frontal bone segment towards cranial. Corresponding to the continuous movement of the beam 44 an overlaid translational and rotational movement is generated. By rotating the two distraction elements 5 the frontal bone segment is tilted and moved towards anterior, as it is on the lingual side pulled towards posterior by the periosteum. Therefore a hinge is not provided in this embodiment, since the periosteum and the musculature of the oral floor take over this function.

In FIG. 8 one end-segment 4 is relating to a fixation element 48 to fixate this segment 4 on the ramus ascendens. This fixation element 48 is composed from a sleeve, which can be slipped over the beam 4 which forms the end segment. On the end of the sleeve a thread is provided. This fixation element 4 can be screwed into the bone at a desired position by means of a screwdriver which is inserting into the sleeve from the free end and which engages via a slot. Subsequently the end segment is inserted into the sleeve and if desired fixated with a set screw which is note depicted.

There has thus been shown and described a novel distraction apparatus for orthodontic, orthognathic and oral/maxillofacial surgery applications on the mandible which fulfills all the objects and advantages sought therefor. Many changes, modifications, variations and other uses and applications of the subject invention will, however, become apparent to those skilled in the art after considering this specification and the accompanying drawing which discloses the preferred embodiment thereof. All such changes, modifications, variations and other uses and applications which do not depart from the spirit and scope of the invention are deemed to be covered by the invention, which is to be limited only by the claims which follow.

What is claimed is:

1. A kit of parts for constructing a distraction appliance for orthodontic/orthognathic and maxillofacial surgery purposes on the mandible for the distraction of an anterior mandibular bone segment above the chin bone against the lower mandibular rim, said bone segment having an upper extremity and a lower extremity, said kit comprising, in combination:

a first distractor module and a second distractor module, wherein the first distractor module is substantially U-shaped and adapted to a dental arch and has a mid-segment and on both sides thereof an end-segment, wherein each end-segment is connected to the mid-segment via a linear distraction element and wherein each end-segment has means for fixating the respective end segment on the mandible and means for fixating the mid-segment to the upper extremity of the bone segment, wherein the second distractor module is connectable to the bone segment above the chin bone and has means for fixating the same at the lower extremity of the bone segment;

wherein the first distractor module and the second distractor module, when fixated on a mandible, are operative together to apply pressure to both the upper and lower extremities of the anterior mandibular bone segment, respectively, to distract the bone segment outward from the lower mandibular rim.

2. A kit of parts for a distraction appliance according to claim 1, wherein the corresponding end-segments of the first distractor module have fixation elements for an attachment on the lateral teeth.

3. A kit of parts for a distraction appliance according to claim 1, wherein the means for fixating the end-segments of the first distractor module include bone screw fixation elements for a screw fixation on the mandible.

4. A kit of parts for a distraction appliance according to claim 1, wherein each distraction element is constructed from at least three elements which are connected to each other, where the first element is screwed inside the second and third element with counter rotational threads such that a rotation of the first element in one or the other sense results in a lengthening or shortening of the distraction element.

5. A kit of parts for a distraction appliance according to claim 4, wherein a section point is provided in the area of each distraction element in which an end-segment thereof can be resolved from the mid-segment.

6. A kit of parts for a distraction appliance according to claim 1, wherein the second distractor module takes the shape of a hinge with two hinge-halves, where one hinge-half is associated with the chin and the other hinge-half to the frontal bone segment to be distracted.

7. A kit of parts for a distraction appliance according to claim 6, wherein the hinge axis is approximately parallel to the occlusal plane and vertical to the sagittal plane.

8. A kit of parts for a distraction appliance according to claim 6, wherein the hinge has a stop position for limiting the rotation range of the hinge-halves.

9. A kit of parts for a distraction appliance according to claim 6, wherein the fixating means include at least one drill hole.

10. A kit of parts for a distraction appliance according to claim 9, wherein the drill hole is a slotted hole.

11. A kit of parts for a distraction appliance according to claim 10, wherein the slotted hole includes a plurality of partially overlapping drill holes such that a plurality of discrete fixation positions are provided.

12. A kit of parts for a distraction appliance according to claim 10, further comprising a guiding sleeve inserted in the slotted hole, which is movable along the slotted hole, and wherein a fixation screw inserted into the guiding sleeve.

13. A kit of parts for a distraction appliance according to claim 12, wherein the guiding sleeve can be clamped inside of the slotted hole.

14. A kit of parts for a distraction appliance according to claim 12, further comprising a cable linkage attached to the guiding sleeve, by means of which linkage the portion bearing this guiding sleeve of the second distractor module can be pivoted around the hinge axis.

15. A kit of parts for a distraction appliance according to claim 14, further comprising a bearing and a screw element held therein for tightening the cable linkage.

16. A kit of parts for a distraction appliance according to claim 6, wherein one hinge-half is V-shaped and wherein fixation parts are provided on the two free ends of the two hinge halves.

17. A kit of parts for a distraction appliance according to claim 14, wherein an additional fixation point is provided at the connection point between the two hinge halves.

18. A kit of parts for a distraction appliance according to claim 1, wherein the second distractor module is pivotally mounted on the mid-segment of the first distractor module.

19. A kit of parts for a distraction appliance according to claim 18, wherein the second distractor module is a cantilever, whereas this cantilever is connected to the mid-segment of the first distractor module and whereas the cantilever has fixation parts for the frontal bone segment.

20. A kit of parts for a distraction appliance according to claim 19, wherein the second distractor module is an U-shaped cantilever with two legs and a mid-segment connecting the two legs, whereas the mid-segment is connected to the mid-segment of the first distractor module and whereas the free ends of the two legs provide fixation parts.

21. A kit of parts for a distraction appliance according to claim 18, wherein the second distractor module is an essentially beam-shaped cantilever which has fixation parts on its free ends.

22. A kit of parts for a distraction appliance according to claim 19, wherein the cantilever can be shortened or lengthened by means of an adaptation mechanism.

23. A kit of parts for a distraction appliance according to claim 22, wherein the adaptation mechanism has a spindle drive with shaft joint.

24. A kit of parts for a distraction appliance according to claim 1, wherein said second distracter module has means for fixating the same at an intact mandibular bone below the bone segment and means for applying distraction pressure to the lower extremity of the bone segment with respect to the intact bone.

* * * * *